United States Patent [19]

Candelon et al.

[11] Patent Number: 5,352,180
[45] Date of Patent: Oct. 4, 1994

[54] METHOD AND APPARATUS FOR REGULATING THE FLOW RATE OF A PERIODIC FLOW HEART PROSTHESIS

[75] Inventors: Bernard J. L. Candelon, Toulon; Jean Trinkl; Patrick J. Havlik, both of Marseille; Jean-Raoul E. Monties, Auriol, all of France

[73] Assignee: Societe Teracor, France

[21] Appl. No.: 917,101

[22] PCT Filed: Feb. 8, 1991

[86] PCT No.: PCT/FR91/00098
§ 371 Date: Sep. 22, 1992
§ 102(e) Date: Sep. 22, 1992

[87] PCT Pub. No.: WO91/12035
PCT Pub. Date: Aug. 22, 1991

[30] Foreign Application Priority Data

Feb. 9, 1990 [FR] France .................. 90 01850
Feb. 9, 1990 [FR] France .................. 90 01851

[51] Int. Cl.5 ............................ A61N 1/362
[52] U.S. Cl. ............................ 600/17; 623/3
[58] Field of Search ................. 600/16, 17; 623/3

[56] References Cited

U.S. PATENT DOCUMENTS 3,911,898 10/1975 Leachman, Jr. ............. 600/17
4,334,180 6/1982 Bramm et al. ............. 600/17 X
4,662,358 5/1987 Farrar et al. ............. 623/3 X Primary Examiner—Lee S. Cohen
Assistant Examiner—Jeffrey R. Jastrzab
Attorney, Agent, or Firm—Ladas & Parry

[57] ABSTRACT

The invention relates to a method and apparatus enabling the blood flow rate conveyed by a heart prosthesis drive by an electrical actuator (18) to be adapted to the flow rate available in the patient's venous return. An apparatus includes a sensor (11) for measuring a physical operating parameter of the prosthesis, and having a passband which extends beyond the variation frequency of the blood flow, and it comprises an angular position sensor (10) for determining the position of the prosthesis, a central unit (15) which receives signals from the sensor (11) and from the angular position sensor (10), which central unit is capable of controlling power supply means (5) of the actuator, and a memory (16) in which normal values of the physical operating parameter of the prosthesis are stored. The apparatus of the invention is particularly intended for monitoring the operation of human heart prostheses.

16 Claims, 6 Drawing Sheets

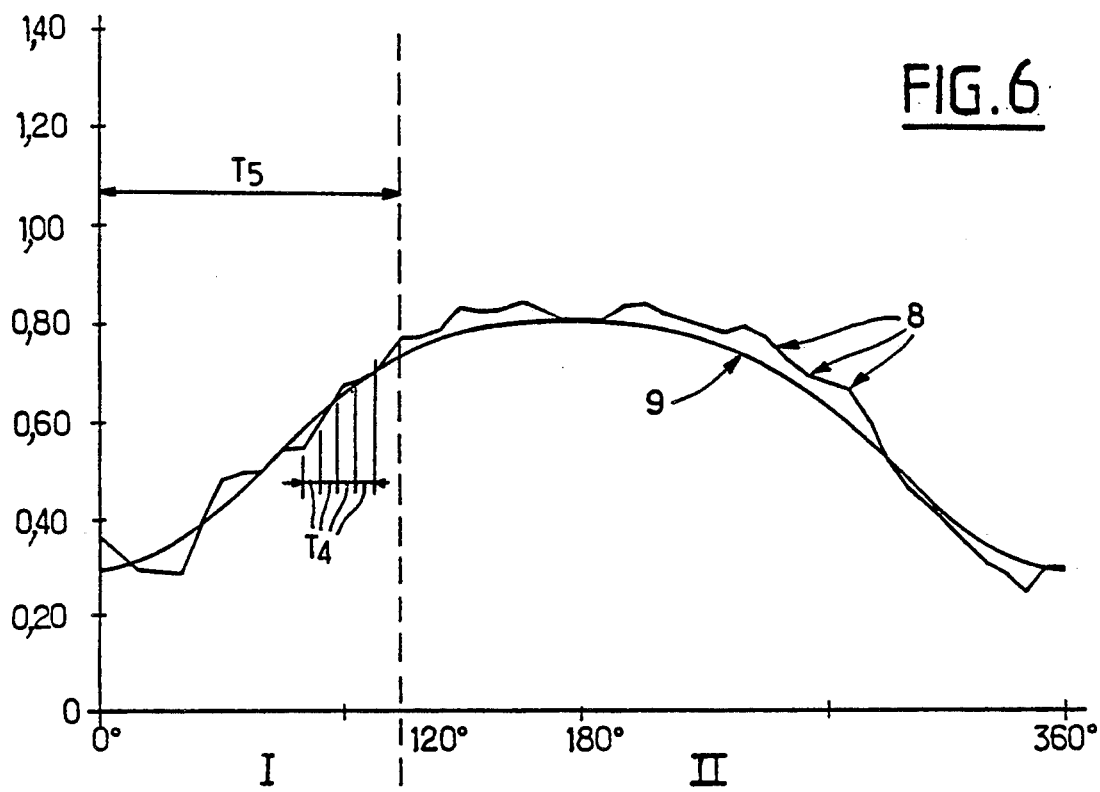
FIG. 6
FIG. 7
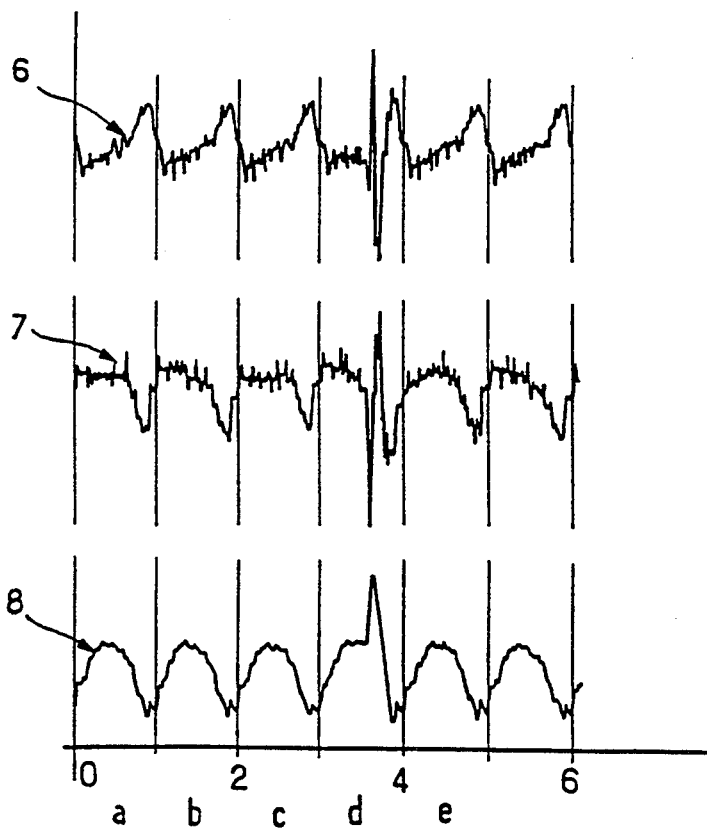
FIG. 7A
FIG. 7B
FIG. 7C

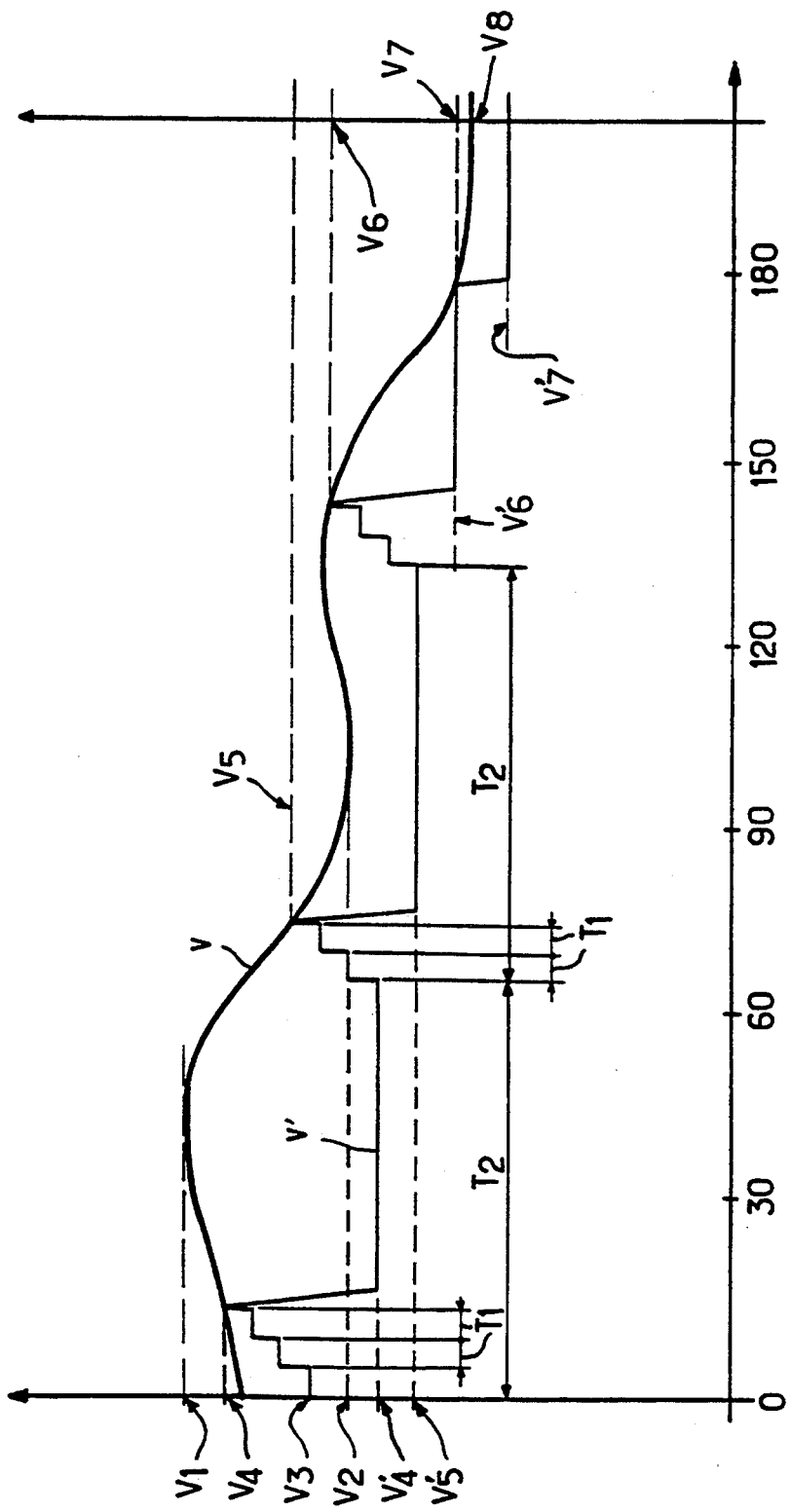

METHOD AND APPARATUS FOR REGULATING THE FLOW RATE OF A PERIODIC FLOW HEART PROSTHESIS

The present invention relates to a method and apparatus for regulating the flow rate of a periodic flow heart prosthesis.

BACKGROUND OF THE INVENTION

Prostheses for heart assistance or replacement are being used more and more to back up or to replace a failing human heart. For assistance purposes, a prosthesis is frequently used to back up half of the heart, the left half or the right half, whereas for replacement purposes, a prosthesis is used that is constituted by two artificial half-hearts. Such a prosthesis always includes at least one pump, an electrical or pneumatic pump drive system, and means for controlling the energy delivered to the drive system to obtain appropriate operation of the prosthesis.

The type of pump used may be a positive displacement pump such as the rotary piston pumps known as the Wankel engine pump or the Cora pump as described in patent FR 2 389 382, membrane pumps, piston pumps, or centrifugal pumps.

The words "pump" and "prosthesis" are used interchangeably below in this document to designate the mechanical device that sucks in and expells the blood of the patient.

In general, such pumps provide a periodic or pulsed flow.

Unless specified otherwise, the term "period" is used below in this document to designate the time interval between the blood flow conveyed by the pump passing on two successive occasions through the same value and in the same direction.

Generally this variation period in the blood flow conveyed by the pump is equal to or is a fraction of the period of the rotary motion of a rotor for rotary pumps or of the translation motion of a piston for piston pumps or membrane pumps.

Pumps are often connected in parallel with a heart or a half-heart that continues to function. Connection to the implantation sites is performed by means of cannulas.

The inlet or admission of the pump is thus connected to the pulmonary or systemic venous return, sometimes via the auricle of the patient's heart, sometimes via the ventricle of the patient's heart.

The flow rate of a prosthesis cannot exceed the flow rate of blood available in the venous return, otherwise there would be a collapse of the blood vessels or a deformation of the valve-forming heart wall or vascular wall, which phenomena must be avoided absolutely.

Devices are known that use pressure sensors for monitoring proper filling of the implantation site from which the prosthesis takes blood by comparing the measured pressure with a reference pressure.

Patent FR 2 470 593 describes a regulator device for a heart prosthesis that includes a plurality of blood pressure servo-controls performed by comparison with a reference pressure.

Those devices measure a mean pressure and are sensitive to variations in physical parameters that may give rise to variations in the measured magnitude without being indicative of a prosthesis misfunction. The parameters that influence these measurements are, in particular, surrounding or atmospheric pressure, and accelerations due to shocks, transport, motion, . . . .

The pressures in the various heart cavities are relative: the reference pressure is the intrathoracic pressure which is itself influenced by the physical environment.

In addition, the amplitude of the pressure variations to be monitored is small compared with the measured magnitude and requires frequent and expensive calibration.

For example, the amplitude of auricular pressure pulses of the right heart lies in the range 0 to about 4 millibars, and for the left heart in the range 0 to about 10 millibars.

It is also known that the heart rate of a patient varies over time, in particular during the day as a function of the patient's metabolism.

Consequently, the drive speed of a heart prosthesis must be capable of adapting to slow changes in heart rate corresponding to said variations in the patient's metabolism.

Until now, these variations have not been monitored by the regulation apparatus, and the drive speed of the prosthesis has been adapted manually and empirically by modifying the reference drive speed.

The problem to be solved is to provide reliable regulation methods and apparatuses for adapting the flow rate conveyed by heart prostheses that provide a periodic flow to the rate at which blood fills the implantation site, such methods and apparatuses being very insensitive to the effects of environmental physical parameters such as atmospheric pressure, or acceleration, and not requiring frequent calibration.

The problem to be solved is also to provide a regulation method and apparatus for a heart prosthesis that is capable of adapting the drive speed of the prosthesis to variations in the metabolism of the patient.

SUMMARY OF THE INVENTION

A solution to the problem posed consists in providing a method of regulating a heart prosthesis which includes a positive displacement pump providing a periodic flow of period T and which includes an electrical actuator driving said pump, said actuator being powered by electrical power supply means, the method which comprises the following operations:

a at least one sensor is provided for measuring a physical operating parameter of said prosthesis and having a passband extending beyond the frequency F corresponding to said period T, and means are provided for determining the angular position of said prosthesis;

b at least one sequence of normal values for said physical operating parameter of said prosthesis is determined together with a sequence of positions of said prosthesis and corresponding to respective ones of said normal values of said physical parameter, which sequence of normal values of said physical parameter should be complied with during said period T;

c at least one threshold S is determined;

then during operation of said prosthesis, during each of said periods, and at time intervals $T_4$ shorter than said period T, and preferably at time intervals $T_4$ that are regularly spaced apart and that are such that the ratio $T/T_4$ is greater than 10;

d values of said physical operating parameter are sensed by means of said sensor and simultaneously the position of said prosthesis is determined by said means;

e a difference is calculated between said sensed value of said physical operating parameter and the normal value of said physical parameter in said sequence of normal values and corresponding to said position of said prosthesis as determined by said means; and f if said difference is greater than said threshold, action is taken on said power supply means to reduce the drive speed of said heart pump.

The said sensor for measuring a physical parameter of the operation of said prosthesis may be a sensor for measuring a parameter of the blood flow caused by said prosthesis, for example the blood pressure or flow rate, alternatively it may be a sensor for measuring a mechanical parameter of the operation of said prosthesis, for example the force exerted by said blood pump on the blood conveyed by said prosthesis or the drive torque applied to said pump by said actuator, or alternatively it may be a sensor for measuring an electrical parameter of the operation of said electrical actuator for driving said prosthesis.

Advantageously, when the drive speed of said pump is changed, timing means of duration $T_1$ are initialized where the ratio $T_1/T$ is less than 500 and is preferably less than 50, and when said time $T_1$ has elapsed, action is taken on said power supply means to increase the drive speed of said heart pump.

Thus, in a preferred mode of using a method of the invention, once said drive speed has been varied in said operation f from a first value to a second value lower than said first value, said timing means are initialized, and when the time of said timing means has elapsed, said drive speed is caused to vary from said second value to said first value, said increase in said drive speed being performed suddenly or progressively.

Advantageously, action is taken on said power supply means at time intervals $T_2$ such that the ratio $T_2/T$ is greater than 1000, to increase, preferably progressively and regularly, the drive speed of said heart pump until said difference obtained in said operation ! is greater than said threshold, thereby determining a maximum drive speed for said pump which corresponds to providing total assistance to a patient.

Advantageously, means are also provided for adjusting a reference value of percentage assistance for a patient, and on detecting said maximum drive speed of said pump corresponding to total assistance, said drive speed of said pump is reduced to a value substantially equal to the product of said maximum speed multiplied by said assistance percentage.

In a first preferred mode of implementing a method of the invention, said sensor for measuring a physical operating parameter is responsive to the fluctuating component of the pressure of a fluid involved in the operation of said heart prosthesis, which sensor is very insensitive to acceleration, and prior to said operation b:

the positions of said pump are sensed over at least one period T and simultaneously the amplitudes are sensed of the fluctuating component of said pressure of said fluid involved in the operation of said corresponding heart prosthesis; and normal values of the fluctuating component of said pressure of said fluid involved in the operation of said heart prosthesis corresponding to said sensed positions are calculated, which values are normally very close to said amplitudes of the fluctuating component of the pressure of said fluid involved in the operation of said heart prosthesis, and lie on a curve which is the graphical representation of a function constituted by a sum of trigonometrical functions whose periods are fractions of said period T, and preferably said heart pump is a rotary heart pump and said positions are angular positions of a rotor of said pump and/or of the rotary motor constituting said actuator, and said sequence of normal values of the fluctuating component of the inlet pressure and also said threshold are recorded in at least one memory.

Alternatively, the said fluid involved in the operation of said prosthesis may be a fluid (preferably a substantially incompressible fluid) which is used in particular in a membrane heart pump as the transmission or drive means for said membrane.

In a second preferred mode of implementing a method of the invention, said sensor for measuring a physical operating parameter is a sensor for an electrical parameter of the operation of said actuator, preferably a sensor responsive to the current taken by said actuator, and in said operation at the beginning of said period, and throughout a duration $T_5$ less than half of said period:

the sensed values of said electrical parameter are used to determine the operating conditions of said heart pump; and said normal values of said electrical parameter that ought to be observed during the present period are predetermined after the said beginning of the period of said duration $T_5$, as a function of said operating conditions and of said sensed values.

Advantageously, said difference is calculated as being the sum of the squares of the differences between said sensed values from the beginning of said period and said normal values of said electrical parameter;

a zero value is given at the beginning of each period to said difference and to said threshold; and said threshold is given a value that varies linearly as a function of the time that has elapsed since the beginning of said period.

The solution to the problem also consists in providing a positive displacement pump providing a periodic flow of period T and which includes an electrical actuator driving said pump, which actuator is powered by electrical power supply means, the apparatus being such that it further includes at least one sensor for measuring a physical operating parameter of said prosthesis and having a passband that extends beyond the frequency F corresponding to said period T, and said apparatus comprises means for determining the position of said prosthesis, at least one memory in which normal values of said physical parameter can be stored, and at least one central unit which receives the signals from said sensor and from said means, which central unit is capable of controlling said power supply means to vary the speed of said actuator and/or of said pump.

Advantageously, said pump is a rotary pump and said actuator is a synchronous motor having permanent magnets, and said means for detecting the position of said prosthesis are Hall effect probe means responsive to the electromagnetic field radiated by said motor, and said pump has its inlet connected to an implantation site and has its outlet connected to the arterial network via cannulas and said passband extends to beyond ten times and preferably beyond 100 times said frequency F.

In a first embodiment of apparatus of the invention, said sensor is a blood pressure sensor situated between said implantation site and said inlet to said pump, which sensor is highly insensitive to acceleration, and normal values of the fluctuating components of the blood pressure at the inlet to said pump are stored in said memory.

In a second embodiment of apparatus of the invention, said sensor is responsive to an electrical parameter of said actuator, and is preferably responsive to the current taken by said actuator.

Advantageously, apparatus of the invention further includes means for adjusting a reference value of assistance percentage for a patient.

The term "fluctuating component" as used in this document relates to the following commonly employed terminology: a time-varying magnitude written G may be broken down as a mean component written $G_1$ and a fluctuating component written $G_2$, which gives rise to the equation: in which $G_1$ is the time mean of G.

$$G = G_1 + G_2$$

in which $G_1$ is the time mean of G.

The invention gives rise to a method and apparatus for regulating the flow rate of a periodic flow heart pump which are insensitive to variations in environmental physical parameters such as atmospheric pressure or acceleration, and which do not require frequent calibration.

An additional advantage provided in particular by said second embodiment of the apparatus is that it avoids the use of an implanted blood pressure sensor thus avoiding the operations that would be required in the event of a fault in an implanted sensor of this type.

The numerous advantages obtained by the invention will be better understood from the following description which refers to the accompanying drawings which show non-limiting examples of apparatuses and methods of the invention.

BRIEF DESCRIPTION OF THE DRAWINGS

FIG. 6 is a graph showing the current taken during one period by the electric motor of a heart pump.

FIG. 7 comprises three graphs 7A, 7B, and 7C.

Graph 7A shows the blood pressure at the inlet to a heart pump during five revolutions or periods.

Graph 7B shows the blood pressure at the outlet of a heart pump during five revolutions or periods.

Graph 7C shows the current taken by the electric motor of said heart pump.

Figure 8:
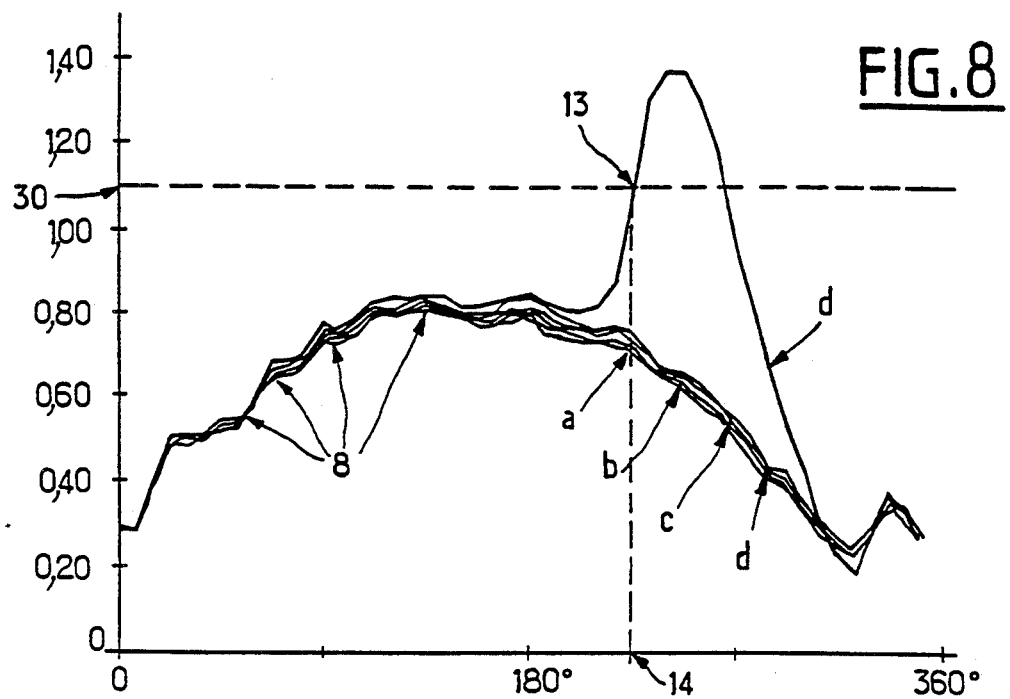

FIG. 8 shows the current taken by said motor during said five periods which are superposed.

Figure 9:
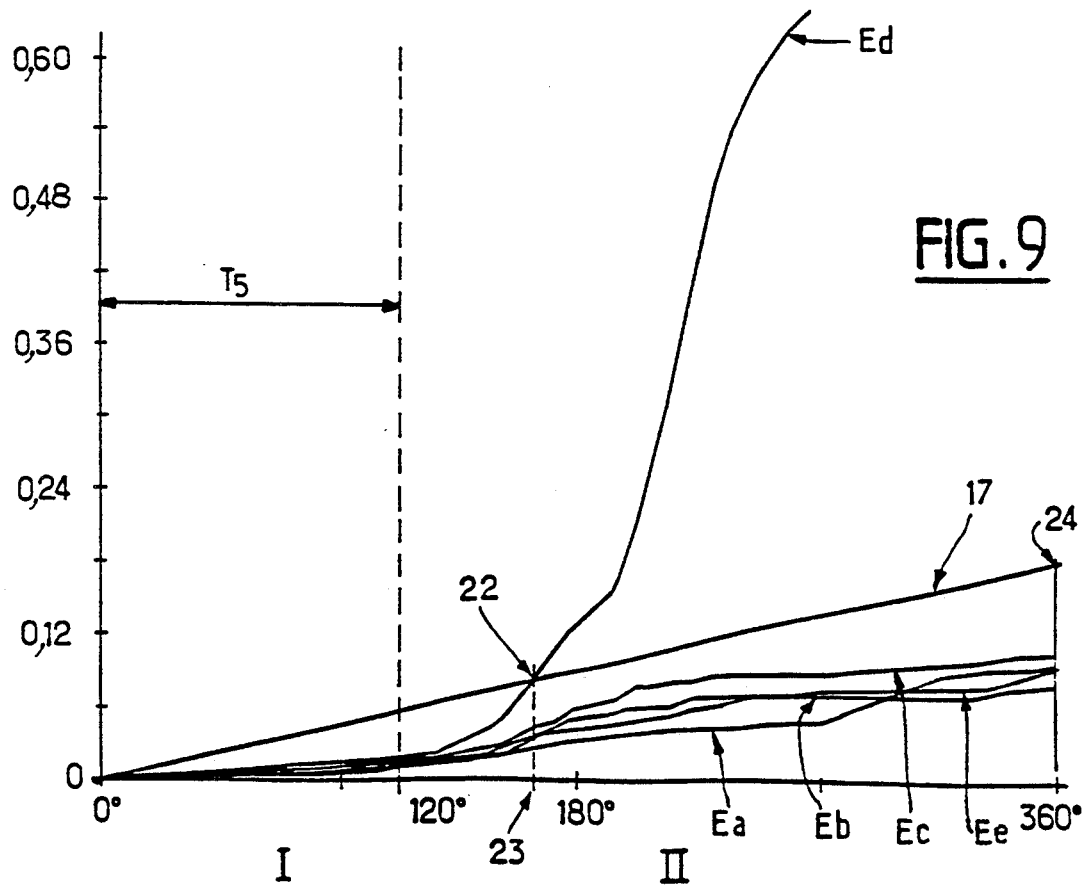

FIG. 9 shows the differences between the current actually taken by the motor and the expected normal current for said five periods.

FIG. 10 shows the operations of a method of the invention.

DETAILED DESCRIPTION OF THE DRAWINGS

Figure 1:
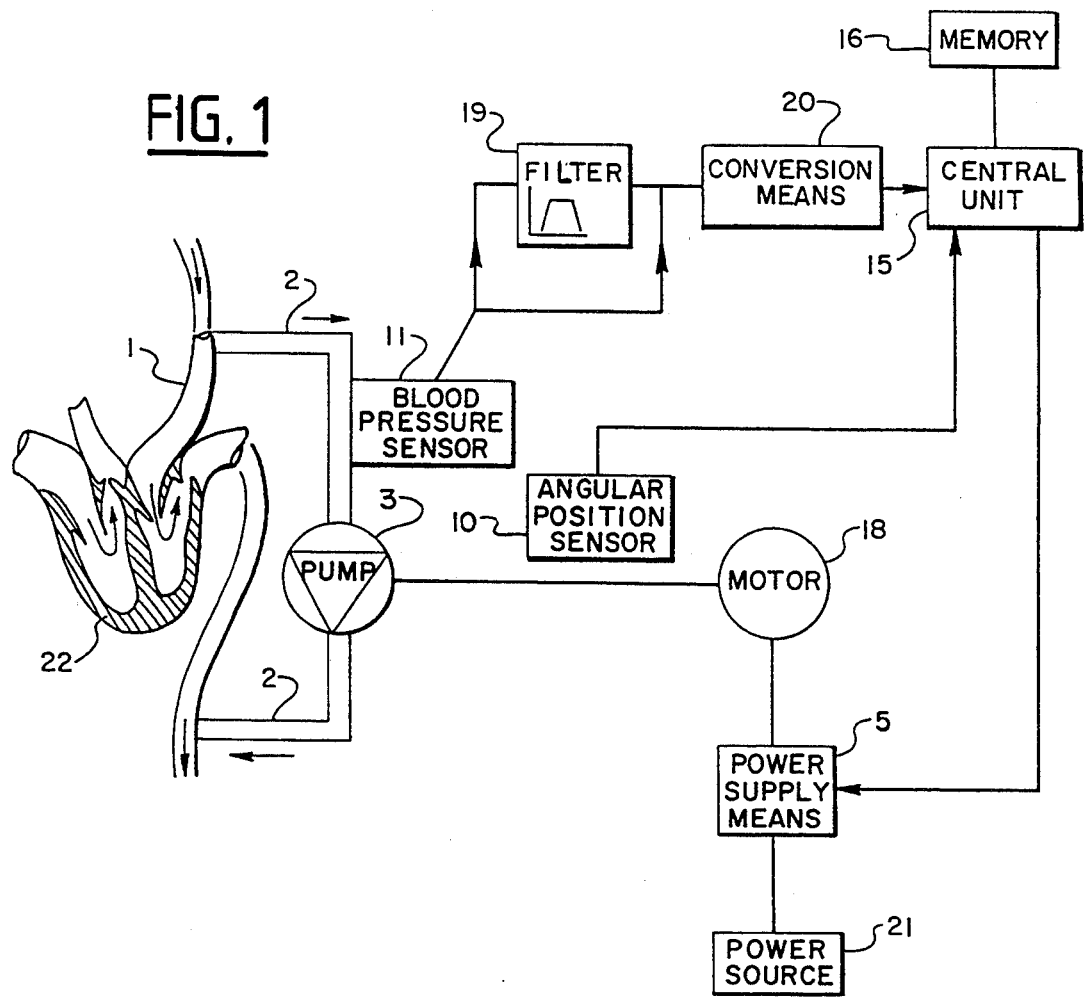
FIG. 1 is a block diagram showing a first embodiment of regulation apparatus of the invention.
Figure 5:
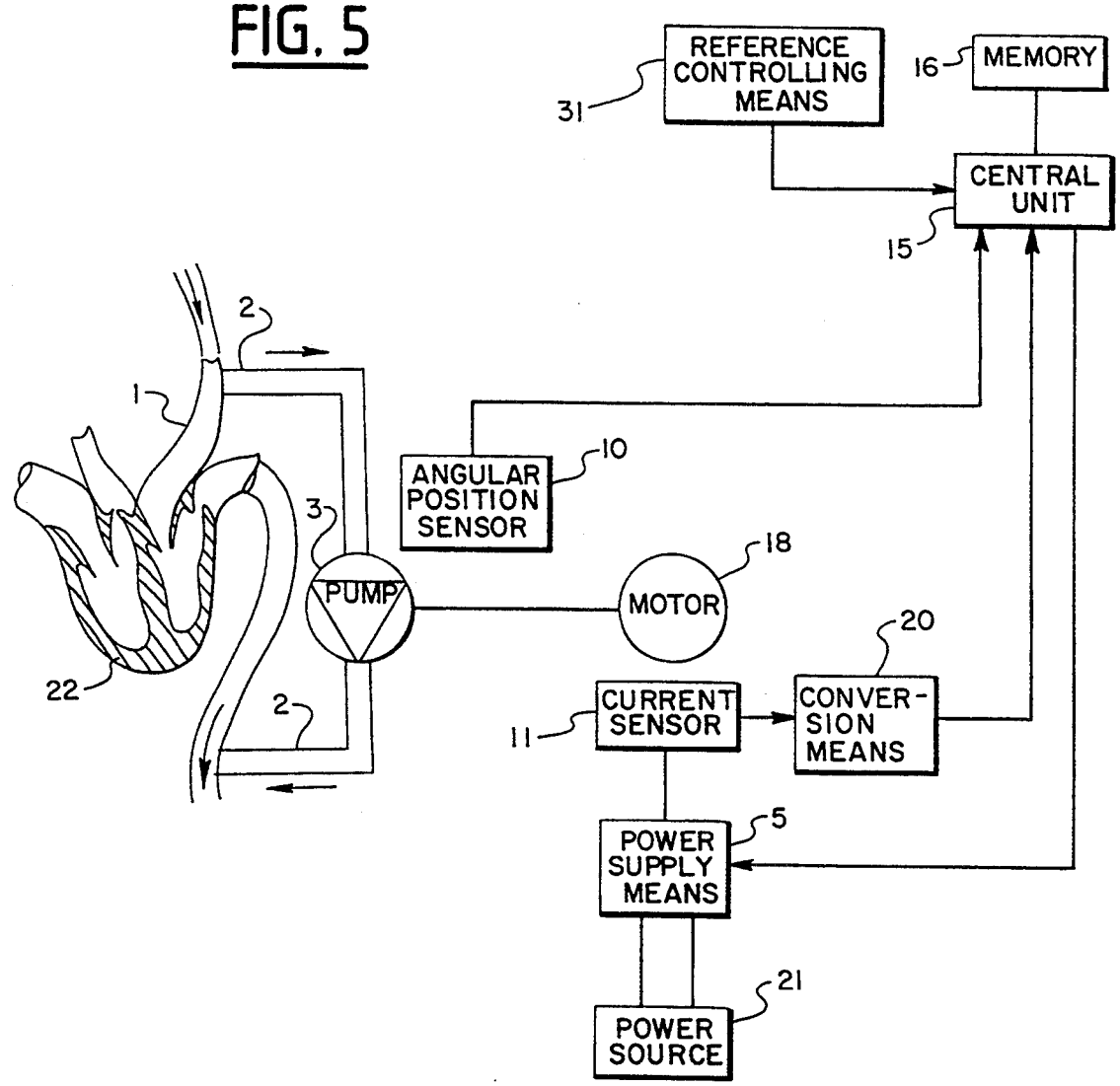
FIG. 5 is a block diagram showing a second embodiment of regulation apparatus of the invention.

FIGS. 1 and 5 show a heart prosthesis constituted by a rotary pump 3 which provides a periodic flow of period T.

Generally the period T has a value close to the mean period of the natural beat of the heart. For example it may lie in the range 250 milliseconds to 2 seconds.

The pump 3 takes blood from a cannula 2 which is connected to the patient's blood system at an implantation site 1. The implantation site 1 may be on the venous return or directly on the auricle of the heart 22.

The said pump 3 expells blood into another cannula 2 which communicates with the arterial network downstream from said heart 22.

As shown in FIGS. 1 and 5, said pump 3 may constitute a prosthesis for assisting one-half of said heart 22 which is capable of continuing to function, or alternatively it could constitute a replacement prosthesis.

The said pump 3 is rotated by a motor 18 which is powered by power supply means 5 themselves connected to a source of energy 21.

For example, the said motor 18 may be a highly compact electric motor without brushes and having permanent magnets, such that the assembly constituted by the pump and its motor can be implanted in the patient.

The said power supply means 5 transform the energy available from said source 21 to deliver energy to the motor suitable for ensuring that it operates properly. Said power supply means may be constituted, for example, by a static polyphase inverter.

The apparatus of the invention may include a rotation sensor 10 which provides a signal corresponding to the angular position of a rotor of the prosthesis, which signal is transmitted to the central unit 15.

The said angular position sensor 10 may be of the resolver type, the synchro-transmitter type, or of the absolute, relative, or incremental encoder type.

Alternatively, an electronic circuit, such as that provided by the company SGS under the reference L6230 or that provided by the company Philips Component under the reference T05414X may be used, making it possible to simulate said Hall effect probes and thus making it possible to determine the angular position of the rotor of said electric motor driving said prosthesis.

Preferably, this sensor has high resolution, which resolution may be greater than 1,000 points per revolution, and it may also be used for servo-controlling the motor 18, nevertheless a resolution of about 48 points per revolution turns out to be satisfactory in many cases.

Such resolution may be obtained in particular by using three Hall effect probes placed in the rotor of an electric motor fitted with a permanent magnet rotor having 16 poles.

In a first embodiment shown in FIG. 1, the apparatus of the invention includes a blood pressure sensor 11 which is a dynamic pressure sensor whose passband extends beyond the frequency corresponding to the period T of the pulses provided by said pump.

This sensor is in contact with the blood flow taken in by the prosthesis and is situated between the implantation site 1 and the intake of said pump 3.

Advantageously, the sensor is situated in said cannula 2 at the inlet of said pump 3.

Advantageously, this pressure sensor is acceleration compensated so as to reduce disturbances in the signal it delivers due to shock. For example, the pressure sensor may be of the piezoelectric type.

In this embodiment of regulation apparatus of the invention, said pressure sensor 11 is connected to said central unit 15 via amplification and conversion means 20 which transform the electric signal delivered by said pressure sensor so as to make it compatible with the interface of said central unit 15.

Advantageously, the signal from said pressure sensor 11 passes through one or more filters 19 which eliminate very high and very low frequency components, which components are not useful to the regulation apparatus and may, under certain circumstances, interfere with flow rate regulation.

Said central unit may be constituted, for example, by an electronics card controlled by a microprocessor. This central unit is connected firstly to an electronic memory 16 which contains the normal values of the fluctuating components of blood pressure at the inlet of the heart pump, and secondly to said power supply means 5 which it controls so as to cause the speed of said heart pump to vary.

Advantageously, said memory 16 may contain various series of normal values of the fluctuating component of the inlet pressure, with each series corresponding to a different type of environment, e.g. to different values of said period T.

Said memory may also contain the values of acceptable differences E between the normal values contained in said memory and the sensed values of the fluctuating components of the blood pressure at the inlet to said heart prosthesis.

The said pressure sensor 11, the said filter 19, the said conversion means 20, the said central unit 15, the said memory 16, and the said power supply means 5 all co-operate in such a manner that in the event of a failure to fill the heart cavity in which said cannula 2 connected to the inlet of said pump 3 is implanted, said failure causing a rapid change in the inlet pressure of the pump, said pressure fluctuation or variation 8 is sensed by said pressure sensor 11, is transmitted to said conversion means 20, possibly after filtering by said filter 19, is then transformed by said means 20 to be compatible with the interface of said central unit 15, which then compares said sensed pressure variation with the normal value 9 stored in the memory 16 and controls said power supply means 5 to reduce the speed of rotation of said prosthesis, thereby reducing the flow rate it conveys, when the difference between said variation 8 and said normal value 9 is greater than a threshold recorded in said memory 16, thereby avoiding collapse of blood vessels or deformation of the walls of the heart cavity.

Figure 2:
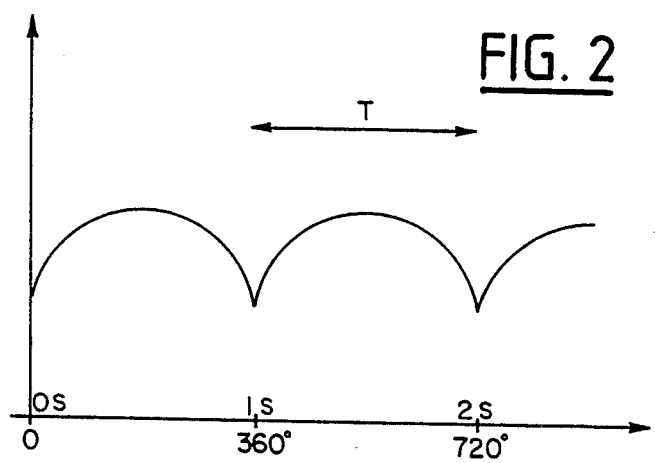
FIG. 2 is a graph showing one example of the waveform of pulses in the blood flow sucked into a positive displacement heart pump.

FIG. 2 shows an example of the appearance of the pulses in the flow at the intake to a rotary piston heart pump.

The abscissa represents time or angular position of a rotor of a prosthesis when driven at constant speed.

The ordinate represents the flow conveyed by said prosthesis.

The curve of FIG. 2 shows normal operation of said heart prosthesis.

In this example, the period T is substantially equal to 1 second.

Figure 3:
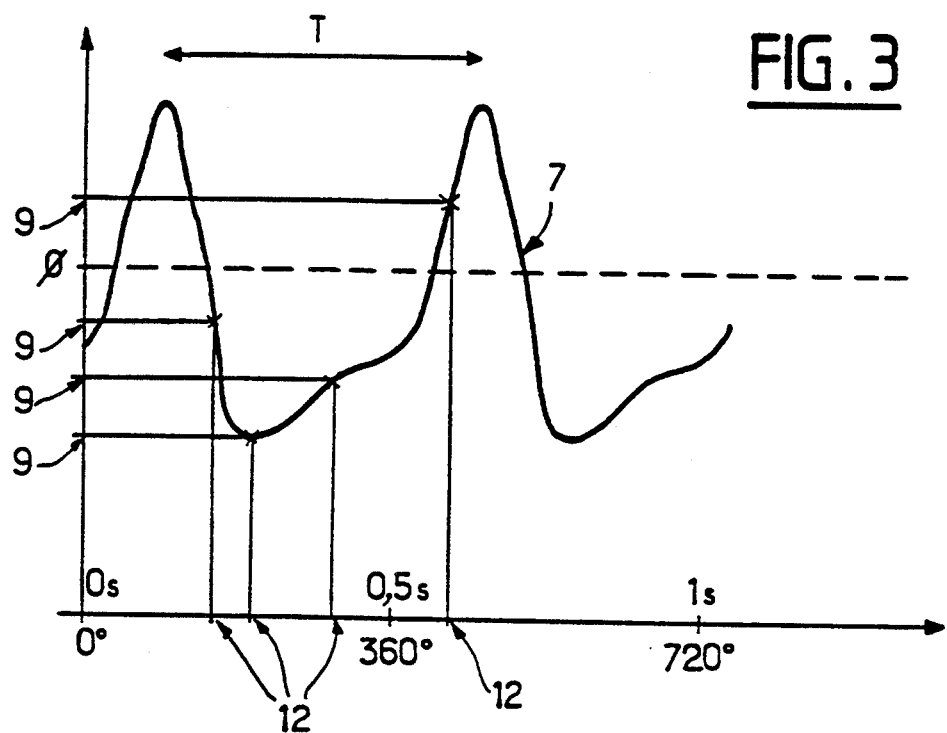
FIG. 3 is a graph showing the main operations in a first stage of a first method of the invention.

FIG. 3 is a graph showing the main operations performed during the first stage of a method of the invention, referred to as the preparatory stage.

The abscissa represents time or angular position of a rotor of the heart prosthesis when driven at constant speed. This axis is graduated in seconds for time and in degrees for angular position.

The ordinate represents blood pressure in the cannula 2 at the location where said pressure sensor is situated.

The period T of variation in the blood flow conveyed by the heart pump is approximately half a second.

The angular positions 12 of a rotor of said heart prosthesis and the normal values 9 of the fluctuating component of the inlet pressure to said heart pump are plotted on the graph for a period T, with each pair of values (9, 12) defining a point on the graph.

A curve 7 is constructed passing through the points defined by said angular positions 12 and said normal values 9 of the fluctuating component in the blood pressure at the inlet to said heart pump.

Advantageously, prior to recording the normal values 9, the angular position 12 and the amplitudes 8 of the fluctuating component of the inlet pressure to the pump are sensed for at least one period T, while ensuring that the operation of the prosthesis is satisfactory.

Said sensed amplitudes 8 are used for calculating normal values 9 of the fluctuating component of the blood pressure at the inlet to the pump, corresponding to said angular positions 12 so that said normal values 9 are close to said sensed values 8.

Advantageously, said normal values 9 are calculated so that they lie on a curve 7 which is a graphical representation of a function expressing variations in the fluctuating component of the inlet pressure to the pump as a function of the angular position of a rotor of the pump, which function is constituted by a sum of trigonometrical functions whose periods are fractions of said period T of the variation in the pump flow.

Advantageously, said angular positions 12 are selected to be regularly spaced apart in the range 0 to 360°.

In a preferred mode of operating the method of the invention, prior to the first stage, the values 13 of the fluctuating component of the normal flow conveyed by the prosthesis are recorded and the normal values 9 of the fluctuating component of the pressure at the inlet to the pump are calculated from said values 13.

Figure 4:
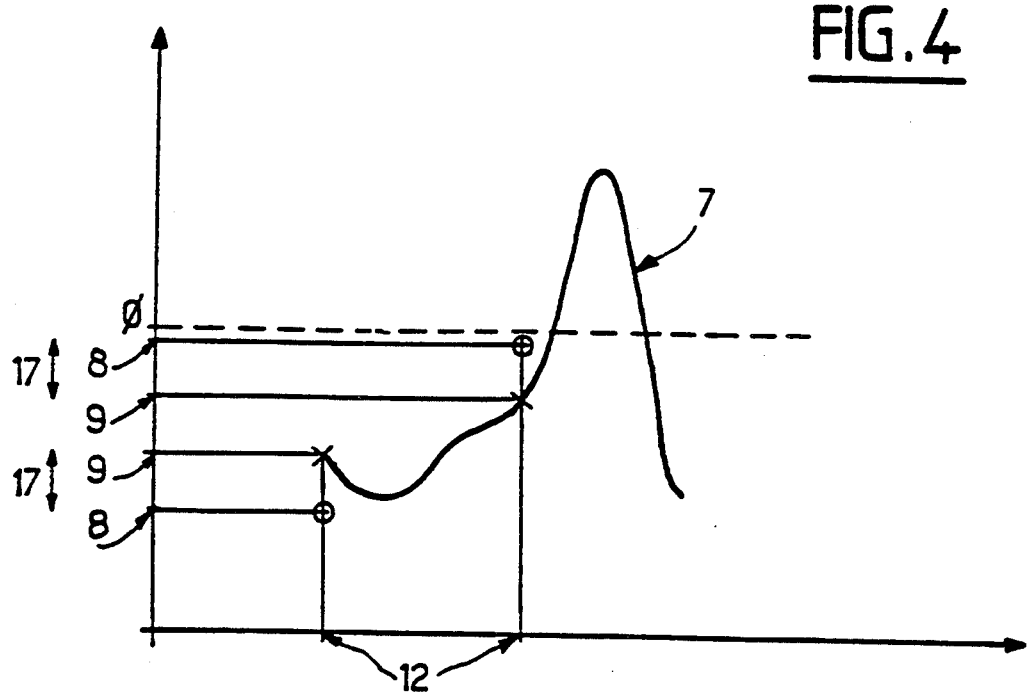
FIG. 4 is a graph showing the main operations of a second stage of a first method of the invention.

FIG. 4 is a graph showing the main operations performed during the second stage of a method of the invention, referred to as the surveillance stage.

The axes represent the same parameters as described for FIG. 3.

Said angular position 12 of said rotor and said amplitude 8 of the fluctuating component of the pressure at the inlet to said pump are sensed simultaneously and plotted on the graph.

Said curve 7 obtained during the preparatory stage is also plotted on the graph.

The difference 17 between said sensed amplitude 8 of the fluctuating component of the inlet pressure and said normal value 9 of the fluctuating component of the inlet pressure is calculated, where the value 9 is the ordinate of the point on said curve 7 whose abscissa corresponds to the sensed angular position 12.

If the absolute value of said difference 17 is greater than said threshold recorded during the preparatory stage, the speed of rotation of the heart pump is reduced so as to reduce its flow rate.

Advantageously, after said amplitude 8 of the fluctuating component of the inlet pressure of the pump has been sensed, low frequency and high frequency components are eliminated therefrom before performing said comparison.

In a particular mode of operation, components are eliminated which have a period which is less than half the period T of variation in the blood flow conveyed by the pump, as are components whose period is greater than five times said period T.

For a heart prosthesis including a piston pump or a membrane pump, said angular position sensor may be replaced by a linear position sensor.

In a second embodiment shown in FIG. 5, apparatus of the invention includes a current sensor 11 whose passband is greater than that of the frequency corresponding to said period T of pulses in the flow through the heart pump.

This sensor measures the current taken by said motor 18. It may be of the resistive type or it may be constituted by at least one Hall effect probe, for example.

Advantageously, this sensor is situated on or is inserted in the electrical circuit connecting said motor 18 to said power supply means 5, and as close as possible to said motor.

In this embodiment of regulation apparatus of the invention, said current sensor 11 is connected to the central unit 15 via amplification and conversion means 20 which transform the electrical signal delivered by said current sensor 11 so as to make it compatible with the interface of said central unit 15. For example the central unit may be an electronics card controlled by a microprocessor. This central unit is connected firstly to an electronic memory 16 which contains the normal values of current taken by the motor 18 of the heart pump, and secondly to the power supply means 5 which it controls so as to vary the speed of the heart pump.

Advantageously, means 31 are also provided for controlling a reference value of assistance percentage, which means may be connected to said microprocessor 15 so that when a drive speed has been measured corresponding to total assistance of a patient, it is possible to define a drive speed reference value corresponding to the heart assistance percentage defined by the medical authority, which percentage may be input and recorded in the apparatus of the invention by said means for adjusting a reference value of the assistance percentage.

Advantageously, the said memory 16 may contain various series of normal current values, each series corresponding to different environmental conditions.

Said memory may also contain the values of differences E that are acceptable between said normal values contained in the memory and the sensed values of the current taken by said motor 18.

In apparatus of the invention, said current sensor 11, said conversion means 20, said central unit 15, said memory 16, and said power supply means 5 all co-operate in such a manner that in the event of a failure to fill the heart cavity in which the cannula 2 connected to the inlet of said pump 3 is implanted, said failure gives rise to a rapid change in the current taken by said motor 18, said current variation 8 being sensed by said current sensor 11, and transmitted to said conversion means 20 where it is transformed by said means 20 so as to be compatible with the interface of said central unit 15, which compares said sensed current variation with said normal value 9 stored in said memory 16 and controls said power supply means 5 so as to reduce the speed of rotation of said prosthesis, thereby reducing the flow conveyed by the prosthesis, in the event that the difference between said current 8 and said normal value 9 is greater than a threshold S recorded in said memory 16, thus avoiding collapse of the blood vessels or deformation of the walls of the heart cavity.

FIG. 6 shows an example of the appearance of variations in the current taken by the motor of a heart pump having a rotary piston.

The abscissa represents time or angular position of a rotor of the prosthesis when driven at constant speed.

This axis is graduated from 0 to 360° which corresponds to one revolution of the rotor of the prosthesis and to one period in the variation of the blood flow conveyed by the prosthesis.

The ordinate represents the current taken by the motor.

The curve of FIG. 6 represents the sensed values 8 of current taken when the heart prosthesis is operating normally.

These sensed values 8 are recorded over a period T.

This period T is divided into two stages I and II.

In the implementation of the method of the invention represented by FIGS. 6 to 9, during the first stage I of duration $T_5$ less than $T/2$, said sensed values 8 of the current taken by the motor are used to determine the operating conditions of said prosthesis that normally have an influence on the current taken by said motor. These conditions are, for example, the blood pressure at the inlet to the pump, the outlet pressure, and the real flow rate conveyed by the pump.

Given the physical and geometrical parameters of said prosthesis which, in particular, condition the appearance of the theoretical curve of variation in the conveyed flow, and also the characteristics of said motor, it is possible to predetermine normal values 9 close to the current taken by the motor that ought to apply during stage II.

These normal values 9 form curve 9 in FIG. 6.

These forecast normal values 9 may advantageously be selected to lie on a curve represented by a simple mathematical function, for example a sum of trigonometrical functions whose periods are fractions of said period T of variation in the flow.

From FIG. 6 it can be seen that said values 8 of said electrical parameter of the operation are sensed at regularly spaced apart time intervals $T_4$ for each corresponding value of said position of said prosthesis, such that said sensor 11 can then be used to sense the values of said physical operating parameter and it is simultaneously possible to use said means 10 to determine the position of said prosthesis, after which it is possible to calculate the difference E between said sensed value of said physical operating parameter and the normal value 9 of said physical parameter from said sequence of normal values corresponding to said position of said prosthesis as determined by said means 10, and if said difference E is greater than said threshold, action may be taken on said power supply means 5 to reduce the drive speed of said heart pump.

FIGS. 7A, 7B, and 7C are three curves 6, 7, and 8 respectively representing: variations in the blood pressure at the inlet to said prosthesis; variations in the blood pressure at the outlet of said prosthesis; and variations in the current taken by said motor driving said prosthesis.

These graphs 7A, 7B, and 7C have the same scale along the abscissa, which is graduated in numbers of revolutions of the rotor of said prosthesis, or in number of periods of variation in the conveyed flow rate.

Five periods are shown and are referenced a to e.

In FIGS. 7A and 7B, the ordinate represents variation in blood pressure.

In FIG. 7C, the ordinate represents current taken by said motor and it is graduated in amps.

Periods a, b, c, and e are representative of proper operation of said prosthesis. Period shows a disturbance which causes a very rapid variation in the pressures at the inlet and at the outlet of said pump and in the current taken by said motor.

FIG. 8 is on a larger scale than FIG. 7 and shows said sensed values 8 of the current taken by said motor of said prosthesis during said periods a to e of FIG. 7C.

In FIG. 8, the graphs of said periods a to e of FIG. 7C are superposed.

The abscissa represents time or angular position of a rotor of the prosthesis. It is graduated from 0 to 360° and it represents one revolution or one period.

The ordinate represents current and it is graduated in amps.

An axis parallel to the abscissa defines a current value 30 which could be the value at which a known device is adjusted for limiting the current taken by the electric motor. It can be seen that this axis intersects the curve of said sensed values 8 corresponding to the period where the disturbance took place at a point 13 whose value on the abscissa is at 14. It can be seen that a known type of current limiter device would not make it possible, even assuming that it acts very rapidly, to change the operating reference value for the prosthesis in time, e.g. a speed reference value, and that it therefore cannot provide effective and reliable regulation of the flow rate through said heart prosthesis.

FIG. 9 shows the operations in an implementation of a method of the invention that enable an anomaly in prosthesis operation to be detected.

The abscissa is used with the same conventions as in FIGS. 6 and 8.

Curves Ea, Eb, Ec, Ed, and Ee relate respectively to said periods a to e.

Curve Ea shows how said difference E between said sensed values 8 and said normal values 9 varies during the period (with reference to FIG. 7C) as described in FIG. 6.

It can be seen that in the first stage I of the period, said difference 19A remains very close to the value zero. During this stage, as described with reference to FIG. 6, the normal values 9 corresponding to the sensed values 8 are calculated or determined.

Said difference Ea increases substantially more quickly during the portion of the curve situated in zone II corresponding to the second stage of a method of the invention, since said normal values are fully predetermined at the end of said phase I and will not be modified again until the following period.

In the example shown in FIG. 9, said differences Ea to Ee are calculated as the sum of the squares of the differences between said sensed values 8 and said normal values 9. Said differences Ea to Ee are given the value zero at the beginning of each corresponding period. In the example shown, said duration $T_5$ of said first stage I is substantially equal to the first third of the period. The duration of said second stage II is equal to the last two-thirds of said period.

It is clear that said differences Ea to Ee could be calculated as a function of the differences between said sensed values 8 and said normal values 9 by using other known methods, e.g. the sum of said differences, or the sum of the absolute values of said differences, which sums could possibly be weighted by coefficients or series of coefficients selected as a function of experimental observations.

The curves Eb to Ee are curves equivalent to said curve Ea, but for the periods b to e respectively, as defined in FIG. 7.

In FIG. 9, there can be seen a straight line 17 which shows the linear change of said threshold S during one period from an initial value of zero at the beginning of the period to a final value at 24.

It can be seen that the curves of said differences Ea to Ec and Ee remain below said threshold straight line 17. During said periods a to c and e, said sensed values 8 in said stage II differ little from said normal values 9 as determined during the corresponding stages I.

However, it can be seen that curve Ed, representative of said period during which a disturbance or loss of pressure occurred, intersects said straight line 17 at a point 22 whose value on the abscissa is given by point 23, and after which it goes well past said threshold. In a method of the invention, action will be taken under such circumstances as from the instant 23 when it is detected that said threshold straight line is exceeded by said difference, said action being taken on said power supply means 5 of said motor of said prosthesis to adapt the blood flow of said heart pump to the venous return. Preferably, the speed of said heart pump will be reduced. Advantageously, action can be taken sufficiently quickly to avoid disturbances or pressure drops such as those shown in FIG. 7A appearing.

In the examples represented by FIGS. 6 to 9, said values 8 of the currents taken by said motor are sensed at regular time intervals (marked $T_4$ in FIG. 6) occurring 48 times per period, for example.

In other methods of the invention, a different electrical parameter is used in the same manner, e.g. voltage or power. Under such circumstances, said current sensor could be replaced by a sensor that matches the electrical parameter under surveillance.

FIG. 10 shows the operations of a preferred implementation of a regulation method of the invention.

The abscissa represents time and is graduated in minutes and the ordinate represents speed of rotation and/or drive applied to said heart pump.

In FIG. 10, a curve v shows how the heart assistance needs of a patient vary as a function of time over a period of about 180 minutes, which needs vary as a function of the metabolism of said patient.

It is known that depending on variations in the metabolism of an individual, the blood flow that needs to be conveyed is subject to variations and consequently the assistance blood flow which may be provided in full or in part by a heart prosthesis also varies over time.

It can be seen in this figure, that the drive speed of a prosthesis as represented by said curve v, which enables a blood flow corresponding to total heart assistance to be provided, increases during a first portion of said curve v up to a theoretical drive speed V1, and then decreases to a value V2 which corresponds substantially to a period of 90 minutes on the abscissa, then increases slightly before decreasing again to a value V8 which corresponds to a level region running on from the 180 minute mark on the time axis at 180 minutes.

FIG. 10 also has a second curve marked v' which shows the appearance of changes as a function of time in the drive speed of a heart prosthesis when applying a regulation method of the invention. Close to the zero on the time axis, it can be seen that an initial speed V3, which may be arbitrary, is provided for driving said heart prosthesis. In the timing chart of FIG. 10, it is assumed that a device is provided in accordance with the invention for regulating a reference value in terms of assistance percentage, and in the example shown in FIG. 10 this value is set to about 80%. Thus, in accordance with the invention, in a first portion of said curve v', said drive speed of said heart prosthesis is increased from said initial value V3 in successive steps of duration $T_1$, where $T_1$ is advantageously such that the ratio $T_1/T$ is less than 500 and is preferably less than 50. It can be seen that said drive speed of said heart prosthesis is thus successively increased until a speed $V_4$ is reached which corresponds substantially to the drive speed of the heart prosthesis that corresponds to a blood flow corresponding to total assistance of said patient.

Because said flow conveyed by said prosthesis operating at said drive speed $V_4$ provides total assistance, a very slight increase in said speed will cause said difference to exceed said threshold in accordance with the invention, thereby making it possible to detect that the present speed, i.e. said speed $V_4$, corresponds to the maximum speed which corresponds to said total assistance. As a result, the drive speed of said pump can then be reduced to a value $V'_4$ which is obtained so that the ratio between said speed $V'_4$ and said speed $V_4$ is equal to said predetermined assistance percentage, i.e. in the example shown in FIG. 10 to about 80%. It can be seen that following said stage during which the speed increases regularly and progressively until said speed $V_4$ is reached, said curve v' representative of the drive speed of said heart prosthesis drops to said value $V'_4$ and can remain at said value for a certain length of time.

In accordance with the invention, after a time $T_2$ such that the ratio $T_2/T$ is greater than 1000 for example, a stage is restarted during which said drive speed of said heart prosthesis is increased, preferably regularly and progressively, in order to be able to detect again said maximum drive speed for said heart prosthesis which corresponds to total cardiac assistance of the patient, which varies in accordance with said curve v.

It can be seen that in the time lapse between marks 60 and 90 on the time scale, the said drive speed is increased in steps each of duration substantially equal to said duration $T_1$ until the increase in said speed causes said difference to exceed the threshold, which event is characteristic of the fact that e speed $V_5$ has been reached which corresponds at that particular moment to the maximum drive speed corresponding to total cardiac assistance. It can be seen that in a method the invention, the said drive speed is again reduced to a value $V'_5$ which is obtained in the same manner as before by having a ratio $V'_5/V_5$ substantially equal to 80%, which is the predetermined cardiac assistance percentage.

It can thus be seen that in accordance with the invention, after another time interval $T_2$, the said drive speed is again increased, preferably progressively and regularly, in steps of duration substantially equal to said duration $T_1$, thereby making it possible to reach a speed $V_6$ which causes said measured difference to exceed speed threshold, which event is characteristic of a seed corresponding to total assistance, whereupon the drive speed of said heart pump is again reduced as shown by the graph v' to a new speed $V'_6$ which is obtained by the ratio $V'_6/V_6$ being substantially equal to aid assistance percentage which in this example is 80%. And it can be seen that in he time lapse situated between mare 150 and 180 of the graph in FIG. 10, the same operation occur while operating at said steady speed $V'_6$ when a difference that exceeds the threshold, this time corresponding to a speed $V_7$ which itself corresponds to total assistance of said patient, such that the drive speed of said prosthesis is reduced to a speed $V'_7$ which is obtained relative to said seed $V_7$ by multiplying said speed $V_7$ by said predetermined assistance percentage.

The regulation methods and apparatuses of the invention can advantageously be applied to a prosthesis such as that described in the following documents:

International Society for Artificial Organs, International Workshop on Rotary Blood Pumps, Obertauern, Austria, Dec. 1-3, 1988, pp. 2 to 27 and pp. 28 to 30 (Proceedings edited by H. Thomas, H. Schima, Bioengineering Laboratory, Ludwig Boltzmann Institut, 2nd Dept. of Surgery, University of Vienna).

We claim:

1. A method of regulating a heart prosthesis which includes a positive displacement pump providing a periodic flow of period T and which includes an electrical actuator driving said pump, said actuator being powered by electrical power supply means, the method comprising following operations:
   a) calculating a sequence of normal values for a physical operating parameter of said prosthesis as a function of a sequence of positions of said prosthesis, each of said positions respectively corresponding to one of said normal values of said physical operating parameter, which sequence of normal values of said physical operating parameter should be complied with during said period T;
   b) then during operation prosthesis, during each of said period of said periodic flow, at time intervals $T_4$ shorter than said period T, and preferably at time intervals $T_4$ that are regularly spaced apart and that are such that the ratio $T/T_4$ is greater than 10;
   c) sensing values of said physical operating parameter of said prosthesis by means of a physical operating parameter sensor; and simultaneously sensing a position of said prosthesis by prosthesis position sensor means;
   d) calculating a difference (E) between said sensed value of said physical operating parameter and the normal value of said physical operating parameter in said sequence of normal values corresponding to said position of said prosthesis as sensed by said prosthesis position sensor means, and
   e) if said difference (E) is greater than a threshold (S), taking action on said power supply means to reduce drive speed of said heart pump.

2. The method according to claim 1, wherein when the drive speed of said pump is reduced, initializing timing means of duration $T_1$, wherein a ration $T_1/T$ is less than 500 and is preferably less than 50, and when said time $T_1$ has elapsed, action is taken on said power supply means to increase the drive speed of said heart pump.

3. The method according to claim 1, further comprising taking action on said power supply means at time intervals $T_2$ such that a ratio $T_2/T$ is greater than 1000, to increase, preferably progressively and regularly, the drive speed of said heart pump until said difference (E) is greater than said threshold (S), thereby determining a maximum drive speed for said pump which corresponds to providing total assistance to a patient.

4. The method according to claim 1 further comprising adjusting a patient assistance percentage reference value 3 by adjusting means, and wherein on detecting said maximum drive speed of said pump corresponding to total assistance, reducing said drive speed of said pump to a value substantially equal to the produce of said maximum speed multiplied by said assistance percentage reference value.

5. The method according to claim 1, wherein said physical operating parameter sensor is responsive to the fluctuating component of pressure of a fluid involved in operation of said heart prosthesis, which physical operating parameter sensor is very insensitive to acceleration, and wherein prior to said operation a):

sensing said positions of said prosthesis over at least one period T and simultaneously sensing amplitudes of said fluctuating component of said pressure of said fluid, and calculated normal values of the fluctuating component of said pressure of said fluid as a function of said sensed prosthesis positions, which normal values are very close to said amplitudes of said fluctuating component of said pressure of said fluid, and which normal values lie on a curve which is a graphical representation of a function constituted by a sum of trigonometrical functions whose periods are fractions of said period T.

6. The method according to claim 5, wherein said pressure of said fluid is a blood pressure measured at an inlet of said pump, wherein said heart pump is a rotary heart pump, and wherein said positions are angular positions of a rotor of said pump and/or angular positions of a rotary motor constituting said actuator, and further comprising recording a sequence of said normal values and said threshold in one memory.

7. The method according to claim 1, wherein said physical operating parameter sensor comprises a sensor for measuring an electrical parameter of operation of said actuator, and wherein in said operation d) at the beginning of said period, and throughout a duration $T_5$ less than half of said period T are the following operations:

using the sensed values of said electrical parameter are used to determine operating conditions of said heart pump, and predetermining said normal values of said electrical parameter observed during each period after beginning of said duration $T_5$, as a function of said operating conditions and or said sensed values of said physical operating parameter.

8. The method according to claim 7 further comprising said difference (E) as being a sum of the squares of the differences between said physical operating sensed values from the beginning of said period and said normal values of said electrical parameter, wherein a zero value is given at the beginning of each period to said difference (E) and to said threshold (S), and wherein said threshold (S) is given a value that varies linearly as a function of the time that has elapsed since the beginning of said period.

9. An apparatus for regulating a heart prosthesis that includes a positive displacement pump providing a periodic blood flow of period T and which includes an electrical actuator driving said pump, which actuator is powered by means for supplying electrical power, further including a physical operating parameter sensor having a passband that extends beyond frequency F corresponding to said period T, the apparatus further comprising means for sensing prosthesis position, one memory in which normal values of said physical parameter are stored, one central unit means for receiving signals from said physical operating parameter sensor and from said means for sensing said prosthesis position, which central unit is further means for controlling said means for supplying the electrical power to vary speed of said actuator and/or of said pump, wherein said physical operating parameter sensor is a blood pressure sensor situated between an implantation site and an inlet of said pump, which physical operating parameter sensor is highly insensitive to acceleration, and wherein normal values of fluctuating components of blood pressure at said inlet of said pump are stored in said memory.

10. An apparatus for regulating a heart prosthesis that includes a positive displacement pump providing a periodic blood flow of period T and which includes an electrical actuator driving said pump, which actuator is powered by means for supplying electrical power, further including at least one physical operating parameter sensor having a passband that extends beyond frequency F corresponding to said period T, the apparatus further comprising means for sensing prosthesis position, one memory in which normal values of said physical parameter are stored, one central unit means for receiving signals from said physical operating parameter sensor and from said means for sensing said prosthesis position, which central unit means is is further for controlling said means for supplying electrical power to vary speed of said actuator and/or of said pump, and wherein said physical operating parameter sensor is responsive to an electrical parameter of said actuator.

11. The apparatus according to claim 10, wherein said pump is a rotary pump and said actuator is a synchronous motor having permanent magnets, and said means for sensing position of said prosthesis are responsive to electromagnetic field radiated by said motor.

12. The apparatus according to claim 10, wherein an inlet of said pump is adapted to be connected to an implantation site, and wherein an outlet of said pump is adapted to be connected to arterial network via canulas and wherein said passband extends to beyond ten times said frequency F.

13. The apparatus according to claim 10 further including means for adjusting a reference value of assistance percentage for a patient, further including means for detecting maximum drive speed of said pump corresponding to total assistance, and including means for reducing drive speed of said pump to a value substantially equal to a product of said maximum speed multiplied by said assistance percentage reference value.

14. The apparatus according to claim 10 wherein an inlet of said pump is adapted to be connected to an implantation site, and wherein an outlet of said pump is adapted to be connected to arterial network via canulas and wherein said passband extends to beyond one hundred times said frequency F.

15. The apparatus according to claim 10 wherein said physical operating parameter sensor is responsive to current taken by said actuator.

16. An apparatus for regulating a heart prosthesis which includes a positive displacement pump providing a periodic flow of period T and which includes an electrical actuator driving said pump, which actuator is powered by means for supplying electrical power, said apparatus further comprising:

a physical operating parameter sensor having a passband that extends beyond frequency F corresponding to said period T;

a prosthesis position sensor;

a central unit means for calculating a sequence of normal values for a physical operating parameter of said prosthesis as a function of a sequence of said prosthesis positions, which sequence of normal values should be complied with during said period T;

a memory for storing said normal values of said physical operating parameter;

said central unit means calculating during each of said period, at time intervals $T_4$ such that the ratio $T/T_4$ is greater than 10, a difference (E) between sensed value of said physical operating parameter and the normal value of said physical operating parameter corresponding to prosthesis position sensed by said prosthesis position sensor, and said central unit means reduced drive speed of said heart pump when said difference (E) is greater than a threshold (S).

* * * * *